(12) United States Patent
Walters et al.

(10) Patent No.: US 6,361,982 B1
(45) Date of Patent: Mar. 26, 2002

(54) REGULATORY GENE FOR CLAVULANIC ACID BIOSYNTHESIS

(75) Inventors: Nicola Jane Walters, Chichester; Barry Barton, Lancing; Alison Jane Earl, Steyning, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 08/491,944
(22) PCT Filed: Jan. 28, 1994
(86) PCT No.: PCT/GB94/00173
 § 371 Date: Aug. 31, 1995
 § 102(e) Date: Aug. 31, 1995
(87) PCT Pub. No.: WO94/18326
 PCT Pub. Date: Aug. 18, 1994

(30) Foreign Application Priority Data

Feb. 2, 1993 (GB) .............................................. 9302041

(51) Int. Cl.⁷ .......................... C12D 7/40; C12D 17/16; C12N 1/21; C07H 21/04
(52) U.S. Cl. .......................... 435/136; 435/43; 435/118; 435/119; 435/120; 435/252.3; 435/252.35; 435/320.1; 536/23.7; 536/24.1
(58) Field of Search .......................... 435/43, 118, 119, 435/120, 136, 252.3, 252.35, 320.1; 536/23.7, 24.1

(56) References Cited

FOREIGN PATENT DOCUMENTS

| EP | 0 349 121 | 1/1990 |
|---|---|---|
| EP | 0 354 624 | 2/1990 |

OTHER PUBLICATIONS

S. Horinouchi, et al., "Primary structure of AfsR, a global regulatory protein for secondary metabolite formation in *Streptomyces coelicolor* A3(2)", *Gene*, 95 p.p. 49–56 (1990).

Juan F. Martin, "Clusters of genes for the biosynthesis of antibiotics: regulatory genes and overproduction of pharmaceuticals", *Chemical Abstracts*, 117, Abstract No. 63796 (1992).

*Primary Examiner*—Elizabeth Slobodyansky
(74) *Attorney, Agent, or Firm*—Zoltan Kerekes; Stephen Venetianer; Charles M. Kinzig

(57) ABSTRACT

DNA comprising a regulatory gene for clavulanic acid biosynthesis. DNA is no greater than 7 kb in length and has the configuration of restriction sites shown in FIG. 1 or a fragment thereof. Use of DNA in a method for producing clavulanic acid in a host.

16 Claims, 8 Drawing Sheets

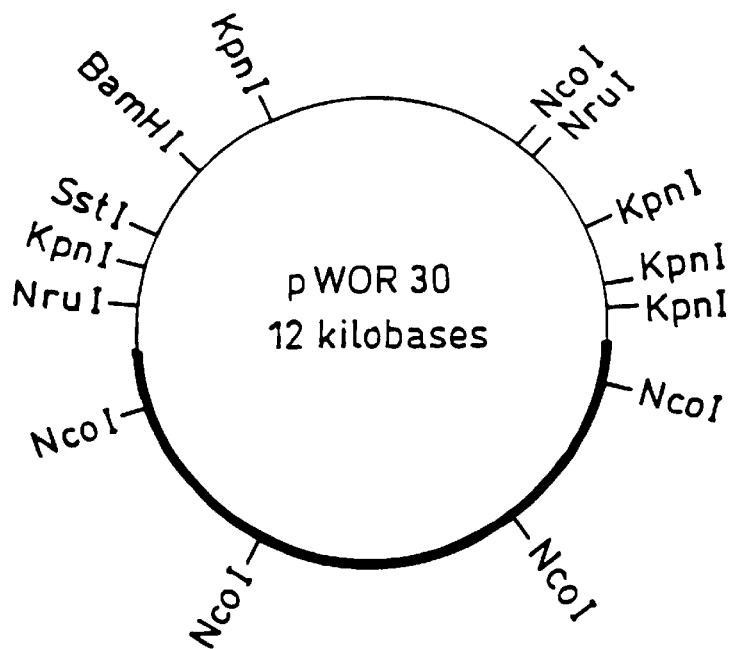
——— DNA derived from S.clavuligerus ATCC 27064
▬▬▬ pIJ680 DNA    FIG. 3
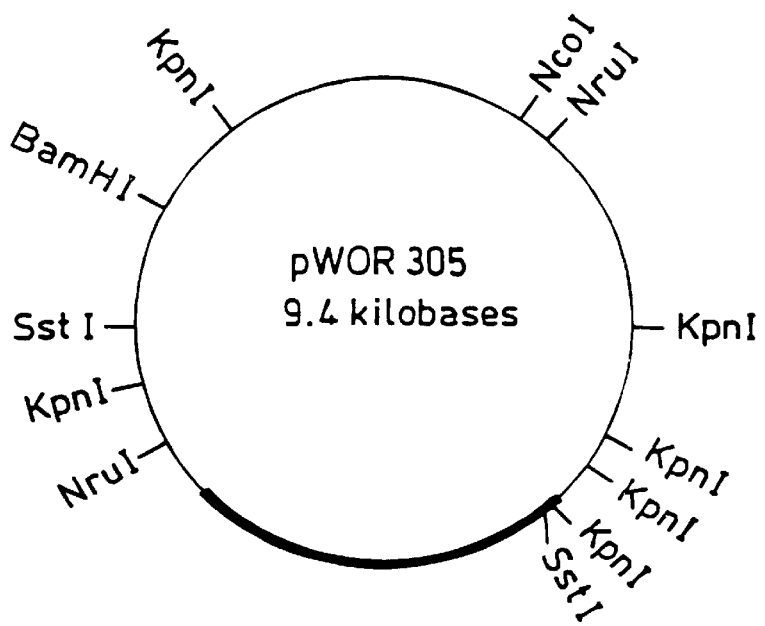
——— DNA derived from S.clavuligerus ATCC 27064
▬▬▬ pIJ2925 DNA    FIG. 4

```
         v10        v20        v30        v40        v50
ggatccgccc aggtccgggg ggtagggagg ggagagtccg acagccccgt
---------+ ---------+ ---------+ ---------+ ---------+ v60        v70        v80        v90       v100
cgacgtccct tcccacagcc ttcccaccca cccgtcccga ctcgccgtga
---------+ ---------+ ---------+ ---------+ ---------+ v110       v120       v130       v140       v150
agccccgggt tcttccgggt tcaccgaggc tgtcccaaat cgtccatgcc
---------+ ---------+ ---------+ ---------+ ---------+ v160       v170       v180       v190       v200
ttgagggtcc cgctgcgtga tcgaaccgta acccttggaa tttctgtgga
---------+ ---------+ ---------+ ---------+ ---------+ v210       v220       v230       v240       v250
ttaagcgtaa acatgggtac cgacaccaag gattacgccg aagccatgtc
---------+ ---------+ ---------+ ---------+ ---------+ v260       v270       v280       v290       v300
cacccctctc ggcgagggcg tggttccttc acaaggggga ccgccATGAA
---------+ ---------+ ---------+ ---------+ ---------+ v310       v320       v330       v340       v350
CACCTGGAAT GATGTGACGA TCCGGCTCCT GGGGCCGGTG ACACTCGTGA
---------+ ---------+ ---------+ ---------+ ---------+ v360       v370       v380       v390       v400
AAGGTTCCGT ACCGATACCC ATCCGCGGGC AGCGACAGCG GCGATTCCTC
---------+ ---------+ ---------+ ---------+ ---------+ v410       v420       v430       v440       v450
GCCTCATTAG CGCTGCGACC GGGCCAGGTC ATCTCCAAGG AAGCGATCAT
---------+ ---------+ ---------+ ---------+ ---------+
```

FIG. 6A

```
         v460       v470       v480       v490       v500
    CGAAGACTCC TGGGACGGGG AGCCACCACT GACCGTTTCG GGCCAGTTGC
    ---------+ ---------+ ---------+ ---------+ ---------+ v510       v520       v530       v540       v550
    AGACGTCGGC CTGGATGATC CGGACCGCGC TGGCGGAGGC GGGGCTGCCC
    ---------+ ---------+ ---------+ ---------+ ---------+ v560       v570       v580       v590       v600
    CGCGACGCCC TCGGCTCCCA CGACCGCGGC TACGAACTGC GCGTCCTGCC
    ---------+ ---------+ ---------+ ---------+ ---------+ v610       v620       v630       v640       v650
    GGACTCCATC GACCTCTTCG TCTTCCGGGA GGCCGTGCGC GCCGTGCGGG
    ---------+ ---------+ ---------+ ---------+ ---------+ v660       v670       v680       v690       v700
    ACCTGCACGC ACGCGGTCAG CACCAGGAGG CGTCCGAACG GCTCGACACG
    ---------+ ---------+ ---------+ ---------+ ---------+ v710       v720       v730       v740       v750
    GCGCTCGCCC TGTGGAAGGG GCCCGCCTTC GCGGATGTGA CCTCCAGTCG
    ---------+ ---------+ ---------+ ---------+ ---------+ v760       v770       v780       v790       v800
    GCTGCGGCTG CGGGGCGAGA CCCTGGAGGA GGAGCGGACC GCCGCGGTCG
    ---------+ ---------+ ---------+ ---------+ ---------+ v810       v820       v830       v840       v850
    AGCTGCGCGC CCTGATCGAT GTCGGCCTCG GCTACTACGG GGACGCGATC
    ---------+ ---------+ ---------+ ---------+ ---------+ v860       v870       v880       v890       v900
    ACCCGGCTGT CGGAGCTCGT CGATCACGAC CCGTTCCGTG AGGACCTGTA
    ---------+ ---------+ ---------+ ---------+ ---------+
```

FIG. 6B

```
           v910       v920       v930       v940       v950
     TGTGAGCCTG ATGAAGGCCT ACTACGCGGA GGGCCGCCAG GCCGACGCGA
     ----------+ ----------+ ----------+ ----------+ ----------+ v960       v970       v980       v990       v1000
     TCCAGGTCTT CCACCGCGCG AAGGACATCC TGCGGGAGCA GATCGGCATC
     ----------+ ----------+ ----------+ ----------+ ----------+ v1010      v1020      v1030      v1040      v1050
     AGCCCCGGCG AGCGGATGAC AAGGGTCATG CAGGCCATCC TGCGTCAGGA
     ----------+ ----------+ ----------+ ----------+ ----------+ v1060      v1070      v1080      v1090      v1100
     CGAGCAGGTC CTGCGGGTCG GTACCCCGGC CTGAaaccgc gcgcgatacg
     ----------+ ----------+ ----------+ ----------+ ----------+ v1110      v1120      v1130      v1140      v1150
     ggaatgtttg tcgacgtttc cctgaaccaa cgctgaagaa acgttcttct
     ----------+ ----------+ ----------+ ----------+ ----------+ v1160      v1170      v1180      v1190      v1200
     tctcacaacg gcggggaatc tccggtcggg aggtgaccgg aggagcctgc
     ----------+ ----------+ ----------+ ----------+ ----------+ v1210      v1220      v1230      v1240      v1250
     gaagacgtac gacccaccgg ccccacccgg gccggccggg ccgagtgccg
     ----------+ ----------+ ----------+ ----------+ ----------+ v1260      v1270      v1280      v1290      v1300
     cccgccgtgc gctccggctc tccttttctt cctcttcttc ctcacacaga
     ----------+ ----------+ ----------+ ----------+ ----------+
```

FIG. 6C

```
           v1310       v1320       v1330       v1340       v1350
     gcagaccgaa aaccaccgcc gcgttcaccc gccggccgta acgtccctcg
     ----------+ ----------+ ----------+ ----------+ ----------+ v1360       v1370       v1380       v1390       v1400
     ctcacagcga tcatcgcgac agcgcgctca ccgagcgcgg ggagcagggg
     ----------+ ----------+ ----------+ ----------+ ----------+ v1410       v1420       v1430       v1440       v1450
     cgacagtggc cgggcggcgg cggacggtac tcaaaggggc cctggcggca
     ----------+ ----------+ ----------+ ----------+ ----------+ v1460       v1470       v1480       v1490       v1500
     tccggtgcgc cggcggtcgg ggcagggctc ggtgtcggcc tcgccggcgc
     ----------+ ----------+ ----------+ ----------+ ----------+ v1510       v1520       v1530       v1540       v1550
     cgacgcgccc gcccgccgcg ggggctcctt ctccacccgg gtgcggctgc
     ----------+ ----------+ ----------+ ----------+ ----------+ v1560       v1570       v1580       v1590       v1600
     gctggctggg ggtctccggc tgggagatcg tcatcgacgg cgggcacagc
     ----------+ ----------+ ----------+ ----------+ ----------+ v1610       v1620       v1630       v1640       v1650
     attctgtttg acccgtatct gagccggatg ccctgccgga atccgcggac
     ----------+ ----------+ ----------+ ----------+ ----------+ v1660       v1670       v1680       v1690       v1700
     gggcgcgctc gattcacggc tgccctgcg gaccgaccgg tcctggtgg
     ----------+ ----------+ ----------+ ----------+ ----------+ v1710       v1720       v1730       v1740       v1750
     aggcgacggc cgcgcgccat ctcaccgttc cgcccgagtt gatcctgatc
     ----------+ ----------+ ----------+ ----------+ ----------+
```

FIG. 6D

```
  1  Met Asn Thr Trp Asn Asp Val Thr Ile Arg Leu Leu   12
 13  Gly Pro Val Thr Leu Val Lys Gly Ser Val Pro Ile   24
 25  Pro Ile Arg Gly Gln Arg Gln Arg Arg Phe Leu Ala   34
 37  Ser Leu Ala Leu Arg Pro Gly Gln Val Ile SEr Lys   48
 49  Glu Ala Ile ILe Glu Asp Ser Trp Asp Gly Glu Pro   60

61  Pro Leu Thr Val Ser Gly Gln Leu Gln Thr Ser Ala   72
 73  Trp Met Ile Arg Thr Ala Leu Ala Glu Ala Gly Leu   84
 85  Pro Arg Asp Ala Leu Gly Ser His Asp Arg Gly Tyr   96
 97  Gly Leu Arg Val Leu Pro Asp Ser Ile Asp Leu Phe  108
109  Val Phe Arg Glu Ala Val Arg Ala Val Arg Asp Leu  120

121  His Ala Arg Gly Gln His Gln Glu Ala Ser Glu Arg  132
133  Leu Asp Thr Ala Leu Ala Leu Trp Lys Gly Pro Ala  144
145  Phe Ala Asp Val Thr Ser Ser Arg Leu Arg Leu Arg  156
157  Gly Glu Thr Leu Glu Glu Glu Arg Thr Ala Ala Val  168
169  Glu Leu Arg Ala Leu Ile Asp Val Gly Leu Gly Tyr  180

181  Tyr Gly Asp Ala Ile Thr Arg Leu Ser Glu Leu Val  192
193  Asp His Asp Pro Phe Arg Glu Asp Leu Tyr Val Ser  204
205  Leu Met Lys Ala Tyr Tyr Ala Glu Gly Arg Gln Ala  216
217  Asp Ala Ile Gln Val Phe His Arg Ala Lys Val Ile  228
229  Leu Arg Glu Gln Ile Gly Ile Ser Pro Gly Glu Arg  240

241  Met Thr Arg Val Met Gln Ala Ile Leu Arg Gln Asp  252
253  Glu Gln Val Leu Arg Val Gly Thr Pro Ala          262
```

FIG. 7

REGULATORY GENE FOR CLAVULANIC ACID BIOSYNTHESIS

CROSS-REFERENCE TO RELATED APPLICATIONS

This application is a 371 of as International Application Number PCT/GB94/00173, filed on Jan. 28, 1994.

BACKGROUND OF THE INVENTION

1. Field of the Invention

This invention relates to recombinant DNA molecules and in particular to recombinant vectors for use in the transformation of a microbial host which contain inserted fragments carrying one or more genes involved in the regulation of clavulanic acid biosynthesis and cephamycin biosynthesis.

Progress in understanding the process of regulation of secondary metabolites produced by micro-organisms such as *Streptomyces clavuligerus* has been slow although it has been established that common control mechanisms may be responsible for the switching on of secondary metabolism in *S. coelicolor*. Two of the secondary metabolites produced in *S. clavuligerus*, clavulanic acid and cephamycin C, are important as antibiotics but appear to have totally unrelated pathways and nothing is currently known of how these pathways are regulated. In particular clavulanic acid is of great clinical value since it is a beta-lactamase inhibitor and protects beta-lactamase-labile beta-lactam antibiotics from degradation. Methods for increasing the yield (titre) of clavulanic acid in fermentation processes are therefore of considerable commercial importance.

2. Description of the Related Art

One approach to the problem of clavulanic acid yield improvement involves the use of recombinant DNA technology using *S. clavuligerus* as the host cell. Several enzymes are believed to be involved in clavulanic acid biosynthesis and the gene or genes encoding a clavaminic acid synthase, which converts one clavulanic acid intermediate, proclavaminic acid, into another one, clavaminic acid, have been cloned (European Patent Application, Publication Number 0 349 121). However, no genes concerned with the regulation of enzymes have so far been identified.

BRIEF DESCRIPTION OF THE DRAWINGS

In order to clearly define the invention reference is made to the accompanying drawings in which:

FIG. 3 is a restriction map of a recombinant plasmid designated pWOR30 created by subcloning the DNA fragment of FIG. 1 into a plasmid pIJ680;

FIG. 4 is a restriction map of a recombinant plasmid designated pWOR305, created by subcloning the DNA fragment of FIG. 1 into a plasmid pIJ2925;

FIG. 6 is the DNA sequence of the open reading frame (ORF) contained within recombinant plasmid pBROC 322 (ORF spans positions 296 to 1082 and is shown in upper case) together with flanking DNA. The insert within pBROC 322 begins at position 1 and ends at position 1751 [SEQ. ID. NO:1]; and FIG. 7 is the deduced amino acid sequence encoded by the ORF of FIG. 6 [SEQ. ID. NO:2].

In the Figures the abbreviations Bcl I, Bgl II etc are conventional abbreviations for restriction endonucleases and the approximate length in kilobases (kb) of the DNA, as determined by sizing experiments carried out by agarose gel electrophoresis, is indicated. It should be understood that the Figures are not intended to show all the restriction sites present on the DNA fragments illustrated.

BRIEF SUMMARY OF THE INVENTION

This invention relates to recombinant DNA molecules and in particular to recombinant vectors for use in the transformation of a microbial host which contain inserted fragments carrying one or more genes involved in the regulation of clavulanic acid biosynthesis and cephamycin biosynthesis.

DETAILED DESCRIPTION OF THE INVENTION

Figure 1:
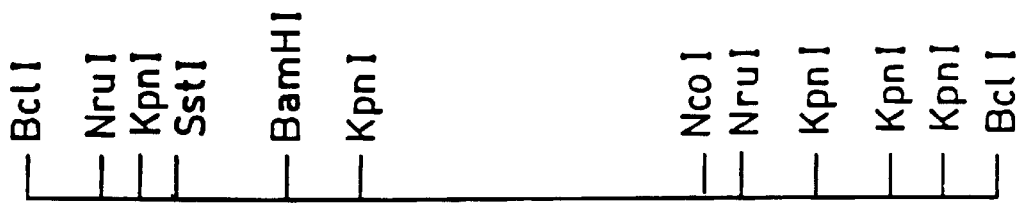
FIG. 1 is a restriction map of a BclI DNA fragment (I) of approximately 7 kb.

According to the present invention there is provided DNA comprising a regulatory gene for clavulanic acid biosynthesis, the said DNA being no greater than about 7 kb in length and comprising a piece of DNA (I) having the configuration of restriction sites shown in FIG. 1 or a fragment thereof.

It will be appreciated that the DNA of the invention is not in its 'natural' state (i.e. as found in the chromosomal DNA of *S. clavuligerus*) but has been purified and isolated to separate it from flanking DNA.

In one preferred aspect the DNA of the invention is DNA (I), having a length of approximately 7 kb and substantially the configuration of restriction sites shown in FIG. 1.

Figure 2:
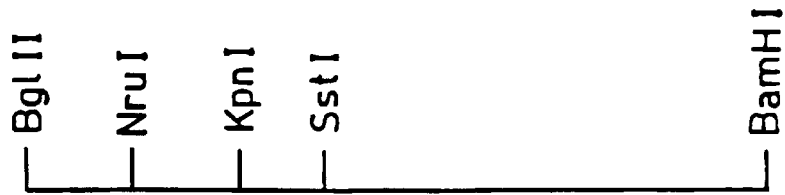
FIG. 2 is a restriction map of a BamHI - BglII DNA fragment (II) of approximately 1.7 kb.

In a further aspect the DNA of the invention is a fragment of (I), especially DNA(II) having a length of approximately 1.7 kb and substantially the configuration of restriction sites shown in FIG. 2.

In yet a further preferred aspect the DNA of the invention has the nucleotide sequence of the open reading frame (ORF) shown in FIG. 6 (SEQ. ID. NO:1)or comprises any nucleotide sequence encoding a protein having substantially the amino acid sequence shown in FIG. 7 (SEQ. ID. NO:2).

In another aspect the DNA of the invention is recombinant DNA.

Preferably the recombinant DNA of the invention comprises a recombinant vector, more preferably a vector capable of transforming and undergoing autonomous replication in a clavulanic acid-producing micro-organism or a vector from which insert DNA can be integrated into the chromosome of the clavulanic acid-producing micro-organism via homologous recombination.

In one aspect the recombinant DNA of the invention is a high expression vector.

The DNA according to any aspect of this invention may be introduced into any suitable vector by methods well known in the art, for example by direct combination of cohesive ends, homopolymer tailing, or by means of a linker or adapter molecule.

Specific examples of such suitable vectors include the following:

(1) pIJ2925, a high copy number *E. coli* vector described by Janssen, G. R. and Bibb, M. J. (1993) Gene, 124, 133–4)
(2) pIJ699, a positive vector for the direct selection of inserts in Streptomyces, as described by Kieser, T. and Melton, R. E. (1988) Gene 65: 83–91.

(3) pIJ680 described by Hopwood et al (1985) Genetic Manipulation of Streptomyces. A Laboratory Manual. The John Innes Foundation.

It will be appreciated that the recombinant vectors prepared according to the above methods may contain the insert DNA in one of two possible orientations. Recombinant vectors containing both orientations are included within the scope of the invention.

Figure 5:
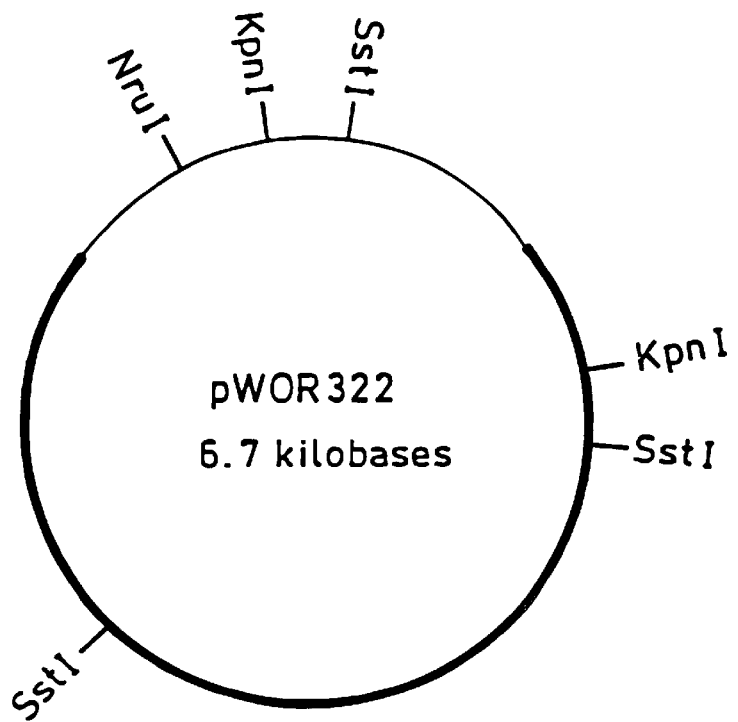
FIG. 5 is a restriction map of a recombinant plasmid designated pWOR322, created by subcloning the DNA fragment of FIG. 2 into a plasmid pIJ699.

Particular recombinant vectors within the scope of the invention include those designated pWOR30, created by subcloning the DNA fragment of FIG. 1 into a plasmid pIJ680 (FIG. 3); pWOR305, created by subcloning the DNA fragment of FIG. 1 into a plasmid pIJ2925 (FIG. 4) and pWOR322, created by subcloning the DNA fragment of FIG. 2 into a plasmid pIJ699 (FIG. 5).

One way to prepare the DNA and recombinant vectors of the invention is to prepare a plasmid comprising the 60 kb segment of S. clavuligerus chromosomal DNA described in FIG. 1 of U.S. Pat. No. 5,759,831. The DNA of the invention may then be obtained by digesting the said plasmid DNA with one or more suitable restriction enzymes. Conveniently the DNA (I) is obtained by preparing a cosmid designated hereinbelow as pBROC371, followed by digestion with BclI as hereinbelow described. Fragments of the DNA (I), for example the DNA (II) or the sequence having the ORF shown in FIG. 6 [SEQ. ID. NO:1], may be obtained from DNA (I) according to methods well known in the art, for example, the DNA(I) may be subcloned into a suitable vector and digested with one or more appropriate restriction enzymes.

A further way to prepare DNA encoding the protein having the amino acid sequence shown in FIG. 7 [SEQ. ID. NO:2], for example the DNA having the ORF shown in FIG. 6 [SEQ. ID. NO:1] or a sequence which is degenerate as a result of the genetic code thereto, is to prepare the desired DNA by synthetic methods using well established methods of oligo and polynucleotide synthesis, preferably by using an automated DNA synthesiser.

The DNA thus prepared or a fragment thereof may, if desired, be used as a probe for probing S. clavuligerus chromosomal DNA (prepared as described in EP 0 349 121) in order to obtain a longer piece of DNA according to the invention comprising the DNA(II), i.e. the DNA fragment (I) or a fragment thereof. Suitable probing techniques are well known in the art.

One utility of the DNA according to the invention is to repair clavulanic acid synthesis in certain empirically derived non-producing mutants of S. clavuligerus, in particular those designated below as dclX and dclZ mutants (specifically dclX68, dclZ124 and dclZ139) which are believed to be 'regulatory mutants', i.e. blocked in one or more genes involved in regulation of clavulanic acid biosynthesis. A further utility of the regulatory DNA of the present invention is to increase titre when introduced into organisms which already produce clavulanic acid.

Clavulanic acid producing organisms include S. clavuligerus ATCC 27064 and derivatives thereof, S. jumoninensis ATCC 29864 and S. katrurahamanus T-272.

The DNA according to the invention may also be used to stimulate the synthesis of clavams in clavam-producing organisms e.g. S. liprmanii.

Accordingly in a further aspect the invention provides a host transformed by a recombinant vector according to the invention.

The host may be transformed by standard techniques such as those described in Hopwood, D. A. et al (1985) Genetic Manipulation of Streptomyces. A Laboratory Manual. The John Innes Foundation or Bailey, C. R. et al. (1984) Biotechnology 2; 808–811.

Preferred hosts are those which are natural producers of clavulanic acid when cultured in an appropriate medium, or regulatory mutants as hereinabove defined, which the DNA according to the invention can repair so that clavulanic acid synthesis is restored and preferably enhanced.

The present invention further provides a method for producing clavulanic acid in a host which is naturally a producer of clavulanic acid or from a suitable non-producing regulatory mutant of a said host, which method comprises the steps of:

(a) transforming the said host or said non-producing mutant thereof with a recombinant vector according to the invention; and (b) culturing the transformants so formed under appropriate conditions so that production of clavulanic acid takes place.

General methods for culturing a clavulanic acid -producing organism so as to obtain clavulanic acid, and methods for purifying the clavulanic acid thus obtained, are set out in UK Patent Specification Number 1, 508, 977.

In the above method the host is preferably S. clavuligerus ATCC 27064 or is derived therefrom.

The following examples illustrate the invention.

EXAMPLES

1. Preparation of chromosomal DNA from dclZ mutants and S.clavuligerus ATCC 27064 and probing with pBROC371 dclZ124 and dclZ139 are both non-producers of products of the clavulanic acid and cephalosporin biosynthetic pathways. These mutants were isolated during random screening procedure for high-titre clavulanic acid producers of S.clavuligerus. They fail to produce clavulanic acid when grown together intimately in co-synthesis tests and have therefore been deemed to be defective in the same gene involved in clavulanic acid biosynthesis. Chromosomal DNA was prepared from both these strains and the wild-type S.clavuligerus 27064 in the following manner.

Spores of both strains were inoculated into 2 shake flasks of Tryptone Soya Broth+maltose growth medium (30 ml/250 ml spring shake flask–Tryptone Soya Broth 30 g/l, maltose 10 g/l) and incubated for 48 hours at 26° C. (with shaking at 240 rpm).

The mycelium was harvested by centrifugation at 1,500 g and washed in 10% sucrose.

The supernatant fraction was poured off and the pellets resuspended in 5 ml lysozyme solution (25 mM Tris pH7.5, 25 mM $Na_2$EDTA pH8.0, 10% sucrose, lysozyme 10 mg/ml) and incubated at room temperature for 30 minutes.

One-tenth volume of lysis solution (1% SDS, 20 mM $Na_2$EDTA) was added and the solution was thoroughly mixed with a wide-bore pipette. Caesium chloride (1.05 g×weight of solution) was dissolved in the solution and a clearing spin (1,500 g) was carried out to remove any precipitated proteins. Ethidium bromide was added to the supernatant to a final concentration of 250 ug/ml and the solution was dispensed into high speed centrifuge tubes.

The tubes were centrifuged in a high speed centrifuge for 20 hours at 55K rpm to create a density gradient and the fraction containing the chromosomal DNA was removed by piercing the tube with a needle and withdrawing the bands containing the highest ethidiun bromide densities.

The sample was extracted with butanol to remove the ethidium bromide and dialysed in an excess volume of TE (10 mM Tris pH8.0, 1 mM $Na_2$EDTA) to remove the caesium chloride. The DNA was precipitated with 0.1 volume of 3M Na acetate pH5.0, 2 volumes of ethanol and redissolved in 2 ml TE after centrifugation.

5-10 ug of chromosomal DNA of 27064, dclZ139 and dclZ-124 were digested with restriction enzymes BamHI, BclI, EcoRI and BglII in a total volume of 30 or 50 ul using standard conditions. The reactions were incubated until examination of a sample of the reaction mix on agarose gel electrophoresis (0.8% gel) showed that the digestions had gone to completion.

The remainder of each sample was then electrophoresed on a 0.8% agarose gel and the DNA was transferred onto a nylon membrane using the standard southern blotting technique [Sambrook, J., Fritsch, E. F., and Maniatis, T., Molecular Cloning. A Laboratory Manual. Second Edition (1989)]. This membrane was probed with the cosmid pBROC371 which contains the 40 kb DNA fragment shown in FIG. 1 of U.S. Pat. No. 6,066,468 having been inserted into the E. coli vector pHC79. DNA was isolated by standard alkaline lysis preparative methods from an E. coli host transformed with this plasmid and purified by caesium chloride gradient [Sambrook, J., Fritsch, E. F., and Maniatis, T., Molecular Cloning. A Laboratory Manual. Second Edition (1989)]. 100 ng of plasmid was radioactively labelled with $^{32}$P (Amersham Multiprime Kit protocol) and used to probe the membrane carrying the separated DNA. Hybridisation was performed at 70° C. for 20 hours in a solution of 6% PEG, 1% SDS, 3×SSC and 100 ug/ml denatured salmon sperm DNA after an overnight prehybridisation in the same buffer (minus the probe). The filter was successively washed in 2×SSC (10' room temperature), 2×SSC (15', 70° C.) twice, 2×SSC, 0.1% SDS (30', 70° C.) and exposed to X-ray film.

Analysis of the autoradiograph showed that the two mutants, dclZ124 and dclZ139, had a deletion of approximately 5.5 kb compared to the wild-type, 27064, in the region of the chromosome from which pBROC371 was derived.

2. Preparation of DNA(I)

About 10 $\mu$g of pBROC371 plasmid DNA was digested with BclI under standard conditions until a sample electrophoresed on an agarose gel showed that the digestion had gone to completion. The remainder of the sample was then electrophoresed on a 0.8% agarose gel and the slice of agarose containing the 7 kb fragment was removed with a razor blade. The DNA was eluted from the gel slice by means of an IBI electroeluter (manufacturers protocol), ethanol-precipitated and redissolved in 20 ul TE. Agarose gel electrophoresis confirmed that the correct fragment had been obtained.

3. Preparation of pWOR30

Spores of an S.clavuligerus strain containing pIJ680 were inoculated into TSB/Maltose medium in a shake-flask and grown up to provide mycelium for a plasmid prep as in Preparation 1. Thiostrepton was added to a concentration of 5 ug/ml to maintain plasmid stability. Plasmid was isolated from the mycelium in a modified version of the Kieser method (T.Kieser, 1984, Plasmid 12:19–36). The mycelium was resuspended in 5 ml of lysozyme solution (0.3M sucrose, 25 mM Tris (pH 8), 25 mM Na$_2$EDTA (pH 8), 2 mg/ml lysozyme) and incubated at 37° C. for 30 minutes. 2.5 ml of 0.3M NaOH, 2% SDS was added with vigorous mixing and the solution was incubated at 70° C., 20 minutes until lysed. The lysate was extracted twice with 800 ul acid phenol/chloroform and the DNA precipitated with unbuffered sodium acetate (3M) and isopropanol. The pellet obtained after centrifugation at 1,500 g was resuspended in 500 ul TE, reprecipitated overnight and finally dissolved in 50 ul TE.

1 ug of pIJ680 plasmid DNA was digested with BamHI and treated with calf intestinal alkaline phosphatase [Sambrook, J., Fritsch, E. F., and Maniatis, T., Molecular Cloning. A Laboratory Manual. Second Edition (1989)]. 250 ng of this DNA and 200 ng of DNA (I) were mixed in a total volume of 10 ul and ligated using standard techniques. 5 ul of the ligation mix was transformed into S.lividans 1326 protoplasts (4×10$^9$/ml) prepared according to standard procedures [Hopwood, D. A. et al (1985) Genetic Manipulation of Streptomyces. A Laboratory Manual. The John Innes Foundation]. After transformation the protoplasts were plated out at dilutions of up to 10$^{-2}$ on to R2YE agar. [Hopwood, D. A. et al (1985) Genetic Manipulation of Streptomyces. A Laboratory Manual.The John Innes Foundations].

After incubation at 30° C. for 24 hours the plates were overpoured with 2 ml soft nutrient broth agar (SNA; 8 g Oxoid Nutrient Broth/l, 3 g agar/l) containing thiostrepton antibiotic at a final concentration of 500 ug/ml to select for plasmid-bearing colonies.

After incubation at 30° C. for three days 19 colonies had appeared on the transformation plates and were transferred onto R2YE medium containing thiostrepton at 50 ug/ml and R2YE containing thiostrepton (50 ug/ml) and neomycin (10 ug/ml) in order to detect those colonies bearing plasmids with inserts in the neomycin gene. 9 colonies failed to grow on the latter plates indicating that the neomycin gene had been disrupted.

Plasmid DNA was prepared from 500 ul of mycelium from 5 of the thiostrepton-resistant, neomycin-sensitive S.lividans 1326 colonies grown as previously described. The mycelium from each colony was incubated in 500 ul lysozyme solution and lysed with 2% SDS. The solution was cleaned by extraction with neutral phenol/cloroform and chloroform and the DNA was then precipitated with ethanol. The chromosomal DNA was removed by spooling on a glass rod and the plasmid DNA was pelleted by centrifugation; the latter was redissolved in 50 ul TE. 20 ul of each plasmid preparation was digested with XhoI restriction enzyme and gel electrophoresis of the samples showed that four of the isolates contained a linear fragment of approximately the expected size, representing pIJ680 (5.3 kb) plus a 7 kb insert.

Further analysis of plasmid DNA by restriction digestion with BcI and double digestion with BamHI/XhoI confirmed that DNA (I) from pBROC371 had been cloned into pIJ680; this construct was called pWOR30 (FIG. 3).

4. Complementation of dclZ124 and dclZ139 with pWOR30 pWOR30 plasmid DNA was used to transform S.clavuligerus dclZ124 and dclZ139 as described in Bailey, C. R. et al (1984) Biotechnology 2:p808–811 except that the protoplasts were incubated at 45° C. for 10 minutes immediately prior to the addition of the DNA. Thiostrepton-resistant transformants were obtained and streaked onto M5D U.S. Pat. No. 5,759,831, medium plus thiostrepton (5 $\mu$g/ml).

Transformants of dclZ124 and dclZ139 with pWOR30 were tested for the repair of clavulanic acid by means of a plate bioassay. Cells of each transformant were stabbed onto M5D and incubated at 26° C. for 6 days. The bioassay plates were then overpoured with soft blood agar (Oxoid) containing a strain of Klebsiella aerogenes described in Reading, C. and Cole, M. (1977) Antimicrob. Agents Chemother. 11:852–7, 0.02% tetrazolium salts and 5 $\mu$g/ml penicillin G. After overnight incubation at 26° C. zones of inhibition had formed around the transformed colonies which were greater than those around the untransformed control (essentially zero).

Those transformants showing zones greater than the control culture were transferred to shake flask culture for accurate titre assessment. Cells from each colony were inoculated into 20 ml of seed medium U.S. Pat. No. 5,759,831 with the addition of thiostrepton (5 $\mu$g/ml final concentration) and grown for 3 days at 26° C. with shaking. 1 ml of the seed culture was then inoculated into a final stage medium U.S. Pat. No. 5,759,831 containing 5 $\mu$g/ml thiostrepton and grown at 26° C. for up to four days. Samples of final stage broth were withdrawn after three or four days growth and assayed for clavulanic acid productivity as described in Bird, A. E. et al (1982) Analyst, 107:1241–1245 and Foulstone, M. and Reading, C. (1982) Antimicrob. Agents Chemother., 22:753–762.

Of the isolates tested, all showed repair of titre, the maximum increase being to 80% of the parent of the clavulanic acid non-producer.

5. Complementation of dclX68 by pWOR30 dclX68 is representative of a number of non-producers of clavulanic acid isolated during random screening for high-titre clavulanic acid producers of S.clavuligerus which fail to produce clavulanic acid when grown together intimately in co-synthesis tests. These mutants differ from dclZ124 and dclZ139 in that they are not deleted for the 5.5 kb region of DNA described in example 1. pWOR30 plasmid DNA was used to transform S.clavuligerus dclX68 as described in example 4.

Thiostrepton-resistant transformants were obtained and streaked onto M5D medium plus thiostrepton (5 $\mu$g/ml)

Transformants of dclX68 with pWOR30 were tested for the repair of clavulanic acid by means of the plate bioassay described in example 4 and showed enhanced zones of inhibition compared to the untransformed control, dclX68. In shake flask fermentations (described in example 4) 11 of the isolates tested showed repair of titre in both the presence and absence of thiostrepton, the maximum increase being to 290% of the parent of the clavulanic acid non-producer.

6. Construction of pWOR305

The 7 kb BclI fragment described as DNA(I) was ligated into a high copy-number E. coli vector, pIJ2925 for further subcloning. 2 $\mu$g of pIJ2925 DNA were digested with BamHI under standard conditions until a sample electrophoresed on an agarose gel indicated that the digestion had gone to completion. The DNA was cleaned up by phenol/chloroform extraction and precipitated with ethanol. The final pellet was dissolved in 30 $\mu$l of TE.

Approximately 50 ng of BamHI-digested pIJ2925 DNA was mixed with 200 ng of DNA (I) in a total volume of 10 $\mu$l and ligated using standard protocols. The resultant ligation mix was used to transform E. coli DH5$\alpha$F' by standard methods. The transformed cells were plated onto L-agar plates supplemented with 50 $\mu$g/ml ampicillin, 12.5 $\mu$g/ml isopropyl-$\beta$-D-galactopyranoside (IPTG) and 40 $\mu$g/ml 5-bromo-4-chloro-3-indolyl-$\beta$-D galactopyranoside (X-gal) to enable visual selection of those colonies containing the pIJ2925 plasmid with an insert.

20 white ampicillin-resistant colonies were obtained and patched onto L-agar plates containing ampicillin (50 $\mu$g/ml). Cells from all of these colonies were inoculated into L-broth containing ampicillin (50 $\mu$g/ml) and grown overnight at 37° C.; plasmid DNA was prepared from 1.5 ml aliquots of the overnight cultures by the standard alkaline lysis method [Sambrook, J., Fritsch, E. F., and Maniatis, T., Molecular Cloning. A Laboratory Manual. Second Edition (1989)]. Restriction digest analysis with KpnI and BamHI confirmed that one isolate contained the 7 kb BclI fragment from pBROC371 in pIJ2925; this construct is called pWOR305 (FIG. 4).

7. Isolation of DNA (II)

pWOR305 plasmid DNA was isolated by standard techniques from a 1 litre E. coli DH5$\alpha$F' culture and purified by caesium chloride gradient. 5 $\mu$g was digested with BamHI and BglII in the same buffer until a sample electrophoresed on an agarose gel showed that the digest had gone to completion. The remainder of the reaction mixture was run on an agarose gel and DNA representing the 1.7 kb BamHI/BglII fragment (DNA (II)), was isolated as described in example 2.

8. Construction of pWOR322

20 $\mu$g of pIJ699, a positive vector for the direct selection of inserts in Streptomyces, was digested with BglII and EcoRI in the same buffer. The 5 kb BglII fragment carrying the Streptomycete functions was isolated as detailed in example 2 for DNA (I) and dissolved in 20 $\mu$l TE.

The plasmid pWOR322 was constructed by ligation of 200 ng of the BglII fragment from pIJ699 with 200 ng of the 1.7 kb BamHI.BglII fragment from pWOR305. 5 $\mu$l of the ligation mix was transformed into protoplasts of S.lividans 1326 as described in example 3 and transformants were selected by overpouring with SNA containing thiostrepton to a final concentration of 50 $\mu$g/ml. Thiostrepton-resistant transformants were obtained and plasmid DNA isolated from this transformant was shown to have the plasmid construct shown in FIG. 5.

9. Restoration of cephalosporin and clavulanic acid biosynthetic pathways in dclX68 by pWOR322 pWOR322 DNA was used to transform protoplasts of dclX68 as described in example 4. Transformants were selected after overpouring with SNA containing 50 $\mu$g/ml thiostrepton and analysed on bioassay for repair of clavulanic acid production as described in example 4, except that the overlay contained 0.003% ampicillin, 0.02% tetrazole and the indicator organism was E. coli JT39 $R_{TEM}$ (Hunter P., et al (1980) J. Antimicrobial Chemotherapy 6:p455–470.). The transformants showed larger zones of inhibition than the negative control and on analysis by shake flask testing (as described in example 4) were found to produce titres greater than the clavulanic acid-producing parent of dclX68. Using HPLC analysis it had been demonstrated that dclX68 was defective in production of products from the cephalosporin biosynthetic pathway. This analysis was performed using a Waters HPLC/Diode Array Detector system with a C18 steel cartridge (Waters 3.9×150 mm) column at room temperature with a flow rate of 1 ml/minute [mobile phase 15% methanol, 85% water, 0.005M tetrabutylammonium hydrogen sulphate (PicA, Waters Registered)]. To detect restoration of the cephalosporin biosynthetic pathway in dclX68/pWOR322 transformants a sample of shake flask fermentation broth from day 4 was centrifuged to remove cellular debris and the supernatents were analysed by HPLC. Restoration of the cephalosporin pathway in the dclX68/pWOR322 transformants was demonstrated by the re-appearance of a known product of the cephalosporin pathway present in the parent of dclX68 but absent in dclX68 itself.

10. Nucleotide sequence of DNA (II)

Using standard techniques several M13mp18 and /or M13p19 vectors constructs were made which contained different subfragments of DNA(II) isolated from pWOR305.

Single-stranded DNA was prepared by standard techniques from all these plasmids and sequenced with the 17 polymerase sequencing kit obtained from Pharmacia. (manufacturer's protocols). Sequencing reactions were separated on 0.8% urea-polyacrylamide sequencing gels and the sequence obtained analysed with the DNASTAR sequencing package.

1751 base pairs of sequence was obtained on both strands covering the entire sequence of DNA (II). One entire open reading frame, which would encode a polypeptide of 262 amino acids, was identified within this sequence (FIG. 6) [SEQ. ID. NO:1]; the protein (FIG. 7) [SEQ. ID. NO:2]

shows homology with other Streptomycete genes implicated in the regulation of secondary metabolites [e.g. actIIorf4, Fernandez-Moreno, M. A., et al. (1991), Cell 66: p769–780 dnrI, Stutzman-Engwall, K. J., et al. (1992) J. Bacteriology 174, 1, p 144–154 afsR Horinouchi, S., et al. (1990) Gene 95: p49–56 reD-orfI, Narva, K. E., and J. S. Feitelson (1990), J. Bacteriology 164: p85–94]. Another feature of this open reading frame is the presence of a rare (in Streptomycete genomes) TTA codon encoding leucine, which has also been implicated in secondary metabolite regulation in *S.coelicolor*. (Leskiw, B. K., Bibb, M. J. and Chater, K. F., (1991) Mol. Microbiol. 5:(12), p2861–2867.

What is claimed is:

1. An isolated DNA obtainable from strain ATCC 27064 comprising a regulatory gene for clavulanic acid biosynthesis, wherein said DNA is no greater than about 7 kb in length and comprises the DNA (I) having the configuration of restriction sites shown in FIG. 1 or a clavulanic acid biosynthesis regulating fragment thereof.

2. The DNA (I) according to claim 1 having a length of approximately 7 kb and the configuration of restriction sites shown in FIG. 1.

3. The DNA fragment of DNA (I) according to claim 1 which is DNA (II) having a length of approximately 1.7 kb and the configuration of restriction sites shown in FIG. 2.

4. The DNA according to claim 1 comprising the nucleotide sequence of the open reading frame (ORF) shown in FIG. 6 (SEQ ID NO: 1).

5. The DNA according to claim 1 comprising a nucleotide sequence encoding a protein having the amino acid sequence shown in FIG. 7 (SEQ ID NO: 2).

6. A DNA which hybridizes with the DNA according to claim 1 and fragments thereof and which codes for a regulatory gene in clavulanic acid biosynthesis, wherein the hybridization is performed on a filter at 70° C. for 20 hours in a solution of 6% PEG, 1% SDS, 3×SSC and 100 ug/ml denatured salmon sperm DNA, and wherein the filter was successively washed in 2×SSC (10 minutes at room temperature), 2×SSC (15 minutes at 70° C.) twice, 2×SSC, 0.1% SDS (30 minutes at 70° C.) and exposed to X-ray film.

7. A recombinant DNA vector comprising the DNA according to claim 1.

8. An isolated protein comprising the amino acid sequence shown in FIG. 7 (SEQ ID NO: 2).

9. A process for transforming a host cell with the DNA according to claim 1 which comprises mixing together the host and the DNA under suitable conditions.

10. A process for transforming a host cell with the vector according to claim 7 which comprises mixing together the host and the vector under suitable conditions.

11. A host cell transformed with the DNA according to claim 1.

12. A host cell transformed with a recombinant vector according to claim 7.

13. A method for producing clavulanic acid in a host which is naturally a producer of clavulanic acid or from a non-producing regulatory mutant of a said host, wherein the mutant is the result of a mutation in the DNA of SEQ ID NO: 1, which method comprises the steps of:

(a) transforming the said host or said non-producing mutant thereof with the DNA according to claim 1; and (b) culturing the transformants so formed under appropriate conditions so that production of clavulanic acid takes place.

14. A method for producing clavulanic acid in a host which is naturally a producer of clavulanic acid or from a non-producing regulatory mutant of a said host, wherein the mutant is the result of a mutation in the DNA of SEQ ID NO: 1, which method comprises the steps of:

(a) transforming the said host or said non-producing mutant thereof with a recombinant vector according to claim 7; and (b) culturing the transformants so formed under appropriate conditions so that production of clavulanic acid takes place.

15. An isolated DNA comprising a nucleotide sequence encoding a protein having the amino acid sequence of SEQ ID NO:2.

16. The isolated DNA of claim 15 comprising the nucleotide sequence of SEQ ID NO: 1.

\* \* \* \* \*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1751 base pairs
      (B) TYPE: nucleic acid
      (C) STRANDEDNESS: double
      (D) TOPOLOGY: unknown (ii) MOLECULE TYPE: DNA (genomic)

(iii) HYPOTHETICAL: NO (vi) ORIGINAL SOURCE:
      (A) ORGANISM: Streptomyces clavuligerus
      (B) STRAIN: S. clavuligerus ATCC 27064

(xi) SEQUENCE DESCRIPTION: SEQ ID NO: 1:

```
GGATCCGCCC AGGTCCGGGG GGTAGGGAGG GGAGAGTCCG ACAGCCCCGT CGACGTCCCT      60

TCCCACAGCC TTCCCACCCA CCCGTCCCGA CTCGCCGTGA AGCCCCGGGT TCTTCCGGGT     120

TCACCGAGGC TGTCCCAAAT CGTCCATGCC TTGAGGGTCC CGCTGCGTGA TCGAACCGTA     180

ACCCTTGGAA TTTCTGTGGA TTAAGCGTAA ACATGGGTGC CGACACCAAG GATTACGCCG     240

AAGCCATGTC CACCCCTCTC GGCGAGGGCG TGGTTCCTTC ACAAGGGGGA CCGCCATGAA     300

CACCTGGAAT GATGTGACGA TCCGGCTCCT GGGGCCGGTG ACACTCGTGA AAGGTTCCGT     360

ACCGATACCC ATCCGCGGGC AGCGACAGCG GCGATTCCTC GCCTCATTAG CGCTGCGACC     420

GGGCCAGGTC ATCTCCAAGG AAGCGATCAT CGAAGACTCC TGGGACGGGG AGCCACCACT     480

GACCGTTTCG GGCCAGTTGC AGACGTCGGC CTGGATGATC CGGACCGCGC TGGCGGAGGC     540

GGGGCTGCCC CGCGACGCCC TCGGCTCCCA CGACCGCGGC TACGAACTGC GCGTCCTGCC     600

GGACTCCATC GACCTCTTCG TCTTCCGGGA GGCCGTGCGC GCCGTGCGGG ACCTGCACGC     660

ACGCGGTCAG CACCAGGAGG CGTCCGAACG GCTCGACACG GCGCTCGCCC TGTGGAAGGG     720

GCCCGCCTTC GCGGATGTGA CCTCCAGTCG GCTGCGGCTG CGGGGCGAGA CCCTGGAGGA     780

GGAGCGGACC GCCGCGGTCG AGCTGCGCGC CCTGATCGAT GTCGGCCTCG GCTACTACGG     840

GGACGCGATC ACCCGGCTGT CGGAGCTCGT CGATCACGAC CCGTTCCGTG AGGACCTGTA     900

TGTGAGCCTG ATGAAGGCCT ACTACGCGGA GGGCCGCCAG GCCGACGCGA TCCAGGTCTT     960

CCACCGCGCG AAGGACATCC TGCGGGAGCA GATCGGCATC AGCCCCGGCG AGCGGATGAC    1020

AAGGGTCATG CAGGCCATCC TGCGTCAGGA CGAGCAGGTC CTGCGGGTCG GTACCCCGGC    1080

CTGAAACCGC GCGCGATACG GGAATGTTTG TCGACGTTTC CCTGAACCAA CGCTGAAGAA    1140

ACGTTCTTCT TCTCACAACG GCGGGAATC TCCGGTCGGG AGGTGACCGG AGGAGCCTGC    1200

GAAGACGTAC GACCCACCGG CCCCACCCGG GCCGCCGGG CCGAGTGCCG CCCGCCGTGC    1260

GCTCCGGCTC TCCTTTTCTT CCTCTTCTTC CTCACACAGA GCAGACCGAA AACCACCGCC    1320

GCGTTCACCC GCCGGCCGTA ACGTCCCTCG CTCACAGCGA TCATCGCGAC AGCGCGCTCA    1380
```

```
CCGAGCGCGG GGAGCAGGGG CGACAGTGGC CGGGCGGCGG CGGACGGTAC TCAAAGGGGC    1440

CCTGGCGGCA TCCGGTGCGC CGGCGGTCGG GGCAGGGCTC GGTGTCGGCC TCGCCGGCGC    1500

CGACGCGCCC GCCCGCCGCG GGGGCTCCTT CTCCACCCGG GTGCGGCTGC GCTGGCTGGG    1560

GGTCTCCGGC TGGGAGATCG TCATCGACGG CGGGCACAGC ATTCTGTTTG ACCCGTATCT    1620

GAGCCGGATG CCCTGCCGGA ATCCGCGGAC GGGCGCGCTC GATTCACGGC TGCCCCTGCG    1680

GACCGACCGG TCCCTGGTGG AGGCGACGGC CGCGCGCCAT CTCACCGTTC CGCCCGAGTT    1740

GATCCTGATC A                                                        1751
```

(2) INFORMATION FOR SEQ ID NO: 2:

(i) SEQUENCE CHARACTERISTICS:
        (A) LENGTH: 262 amino acids
        (B) TYPE: amino acid
        (D) TOPOLOGY: unknown (ii) MOLECULE TYPE: protein (iii) HYPOTHETICAL: YES (vi) ORIGINAL SOURCE:
        (A) ORGANISM: Streptomyces clavuligerus
        (B) STRAIN: S. clavuligerus 27064

(xi) SEQUENCE DESCRIPTION: SEQ ID NO: 2:

```
Met Asn Thr Trp Asn Asp Val Thr Ile Arg Leu Leu Gly Pro Val Thr
1               5                   10                  15

Leu Val Lys Gly Ser Val Pro Ile Pro Ile Arg Gly Gln Arg Gln Arg
                20                  25                  30

Arg Phe Leu Ala Ser Leu Ala Leu Arg Pro Gly Gln Val Ile Ser Lys
            35                  40                  45

Glu Ala Ile Ile Glu Asp Ser Trp Asp Gly Pro Pro Leu Thr Val
    50                  55                  60

Ser Gly Gln Leu Gln Thr Ser Ala Trp Met Ile Arg Thr Ala Leu Ala
65                  70                  75                  80

Glu Ala Gly Leu Pro Arg Asp Ala Leu Gly Ser His Asp Arg Gly Tyr
                85                  90                  95

Glu Leu Arg Val Leu Pro Asp Ser Ile Asp Leu Phe Val Phe Arg Glu
            100                 105                 110

Ala Val Arg Ala Val Arg Asp Leu His Ala Arg Gly Gln His Gln Glu
        115                 120                 125

Ala Ser Glu Arg Leu Asp Thr Ala Leu Ala Leu Trp Lys Gly Pro Ala
    130                 135                 140

Phe Ala Asp Val Thr Ser Ser Arg Leu Arg Leu Arg Gly Glu Thr Leu
145                 150                 155                 160

Glu Glu Glu Arg Thr Ala Ala Val Glu Leu Arg Ala Leu Ile Asp Val
                165                 170                 175

Gly Leu Gly Tyr Tyr Gly Asp Ala Ile Thr Arg Leu Ser Glu Leu Val
            180                 185                 190

Asp His Asp Pro Phe Arg Glu Asp Leu Tyr Val Ser Leu Met Lys Ala
        195                 200                 205

Tyr Tyr Ala Glu Gly Arg Gln Ala Asp Ala Ile Gln Val Phe His Arg
    210                 215                 220

Ala Lys Val Ile Leu Arg Glu Gln Ile Gly Ile Ser Pro Gly Glu Arg
225                 230                 235                 240
```

-continued

```
Met Thr Arg Val Met Gln Ala Ile Leu Arg Gln Asp Glu Gln Val Leu
            245                 250                 255
Arg Val Gly Thr Pro Ala
            260
```